(12) United States Patent
Bhattacharyya et al.

(10) Patent No.: US 10,105,204 B2
(45) Date of Patent: Oct. 23, 2018

(54) IMPLANTS, TOOLS, AND METHODS FOR TREATMENT OF PELVIC CONDITIONS

(71) Applicant: Boston Scientific Scimed, Inc., Maple Grove, MN (US)

(72) Inventors: Shayan Bhattacharyya, Edina, MN (US); Allison R. Brouckman, Somerville, MA (US); Hilary A. Johnson, Portland, OR (US); Lorin S. Paley, Steamboat Springs, CO (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 192 days.

(21) Appl. No.: 15/183,640

(22) Filed: Jun. 15, 2016

(65) Prior Publication Data

US 2016/0374789 A1 Dec. 29, 2016

Related U.S. Application Data

(60) Provisional application No. 62/184,640, filed on Jun. 25, 2015.

(51) Int. Cl.
*A61F 2/00* (2006.01)

(52) U.S. Cl.
CPC ...... *A61F 2/0045* (2013.01); *A61F 2250/003* (2013.01); *A61F 2250/0007* (2013.01); *A61F 2250/0012* (2013.01)

(58) Field of Classification Search
CPC ........ A61F 2250/0007; A61F 2250/003; A61F 2/0045; A61F 2250/0012
See application file for complete search history.

(56) References Cited

U.S. PATENT DOCUMENTS

| | | |
|---|---|---|
| 4,969,892 A | 11/1990 | Burton et al. |
| 5,112,344 A | 5/1992 | Petros |
| 5,474,518 A | 12/1995 | Farrer Velazquez |
| 5,611,515 A | 3/1997 | Benderev et al. |
| 5,669,935 A | 9/1997 | Rosenman et al. |
| 5,842,478 A | 12/1998 | Benderev et al. |
| 5,860,425 A | 1/1999 | Benderev et al. |
| 5,899,909 A | 5/1999 | Claren et al. |
| 6,039,686 A | 3/2000 | Kovac |
| 6,042,534 A | 3/2000 | Gellman et al. |
| 6,110,101 A | 8/2000 | Tihon et al. |
| 6,117,067 A | 9/2000 | Gil-Vernet |
| 6,911,002 B2 | 6/2005 | Fierro |
| 7,364,541 B2 | 4/2008 | Chu et al. |
| 7,422,557 B2 | 9/2008 | Arnal et al. |

(Continued)

*Primary Examiner* — Christine H Matthews
*Assistant Examiner* — Joshua D Lannu
(74) *Attorney, Agent, or Firm* — Bookoff McAndrews, PLLC (57) ABSTRACT

Implants, tools, devices, systems, and related methods for treating pelvic conditions are disclosed, some of which provide support to body tissue to alleviate incontinence. An exemplary implant may comprise a tissue support portion adapted to be positioned to support any one of the urethra or anus, first and second end portions extending form the tissue support portion through body tissue, and an adjustment mechanism acting on or within one or both of the end portions. The adjustment mechanism may comprise one or more of a adjustment element and an adjustment mechanism coupled to the adjustment element.

15 Claims, 5 Drawing Sheets

(56) References Cited

U.S. PATENT DOCUMENTS

| | | |
|---|---|---|
| 7,500,945 B2 | 3/2009 | Cox et al. |
| 7,914,437 B2 | 3/2011 | Gozzi et al. |
| 8,518,061 B2 | 8/2013 | Benderev |
| 8,628,465 B2 | 1/2014 | Mamo et al. |
| 8,771,168 B2 | 7/2014 | Gozzi et al. |
| 2005/0250977 A1 | 11/2005 | Montpetit et al. |
| 2006/0058574 A1 | 3/2006 | Priewe et al. |
| 2009/0259092 A1* | 10/2009 | Ogdahl ............... A61F 2/0045 600/30 |
| 2010/0256442 A1 | 10/2010 | Ogdahl et al. |
| 2012/0316386 A1* | 12/2012 | Wirbisky ........... A61B 17/0401 600/30 |

* cited by examiner

IMPLANTS, TOOLS, AND METHODS FOR TREATMENT OF PELVIC CONDITIONS

CROSS-REFERENCE TO RELATED APPLICATIONS

This patent application claims the benefit of priority under 35 U.S.C. § 119 to U.S. Provisional Patent Application No. 62/184,640, filed Jun. 25, 2015, the entirety of which is herein incorporated by reference.

FIELD OF THE INVENTION

The present disclosure relates generally to implants, tools, devices, systems, and related methods for treating pelvic conditions including but not limited to incontinence conditions in men and women and particularly to implants having mechanisms for selectively adjusting the tension applied through the implant to body tissue.

BACKGROUND

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor.

Urinary incontinence can further be classified as including different types, such as stress urinary incontinence ("SUI"), urge urinary incontinence, and mixed urinary incontinence, among others. Urinary incontinence can be characterized by the loss or diminution in the ability to maintain the urethral sphincter closed as the bladder fills with urine. Male or female SUI generally occurs when the patient is physically stressed.

A sling may be used to treat incontinence and prolapse. These slings typically comprise a central portion that is adapted to support the urethra, two end portions bracketing the support portion, a protective sheath or sheaths encasing at least the end portions, and connectors at the ends of the sling. Various ways of attaching sling ends to sling implantation tools are disclosed in U.S. Pat. Nos. 7,364,541 and 7,500,945; and U.S. Patent Pub. No. 2005/0250977, the entireties of which are herein incorporated by reference. Sling implantation tools are employed to form tissue pathways extending, for example, from a vaginal incision to one more abdominal skin incisions.

Tension in the sling is typically adjusted during an implantation procedure in a manner to take up slack in the sling, impart desirable and efficacious tension, and position the supported tissue. For example, sling tension is typically adjusted at implantation sufficiently to take up any slack in the sling and impart at least a degree of increased tension to the urethra with the bladder empty. Alternative tension adjustment techniques that may be employed during implantation are disclosed in the above-referenced patents and publications.

Typically, such slings are fabricated of a loose weave sling fabric or mesh that acutely engages tissue and encourages tissue ingrowth along the pathway through mesh pores to achieve chronic stabilization or "self-fixation." Tissue ingrowth takes about 2-3 weeks in the typical patient in the absence of any significant intentional or unintentional movement of the mesh. During this post-operative time, the patient monitors the degree of success achieved in ameliorating leakage and any discomfort that might occur if the applied tension is so high as to unduly slow voluntary urination. If any such problems occur, it may be necessary to reopen the incisions to access and pull on the sling ends to tighten the sling central portion around the urethra or to reopen the vaginal incision to pull on the sling central portion to loosen the sling central portion around the urethra. Several approaches have been taken to simplify or reduce the need for such post-operative adjustments.

One tension adjustment complication arises from the fact that the loose weave sling mesh inherently stretches and elongates when tension is applied at the ends or tissue support portion to overcome resistance of the tissue bearing against the sling mesh along the tissue pathway. It is difficult to judge just how much tension to apply to achieve adequate tightening or loosening in the tissue support portion. An elongated repositioning means, e.g., an elongated inextensible tensioning member, may be incorporated, said means extending in or along the sling mesh from near the sling ends to or through the sling central portion. Tension applied to the repositioning means is transmitted along the length of the sling so the sling mesh does not substantially stretch during initial positioning and any repositioning during the acute healing phase.

Other approaches that enable increasing tension of the sling central portion against the urethra involve shortening the lengths of the sling end portions. Mesh folds are formed in the sling end portions using filaments that extend through vaginal incisions externally of the body. Depending on the embodiment, the mesh folds can be released to decrease sling tension or be tightened to increase sling tension by pulling on the filament ends following the initial implantation procedure. In other embodiments, filaments are extended substantially through the lengths of the sling end portions and extend from the vaginal incisions. The filaments may be gripped and pulled to tighten the mesh in the sling end portions to increase overall sling tension.

In still another approach disclosed, for example, in U.S. Patent Pub. No. 2006/0058574, the entirety of which is herein incorporated by reference, a mesh sling or tape is further modified to include a mechanical adjustment means to adjust the length of the tape in the end portions on either side of the central portion after the tape has been implanted in the tissue pathways. The mechanical adjustment means may incorporate a tie-wrap mechanism or sutures and one-way suture retaining devices of the type disclosed in U.S. Pat. No. 5,669,935, the entirety of which is herein incorporated by reference, wherein said means is located along the tape on either side of the central portion. In each case, one suture end is affixed to the tape and extends along it and through a suture retaining device affixed to the tape closer to the central portion. The sutures or tie-wrap are not tensioned at implantation, and the tie-wrap or suture free ends extend through the vaginal incision. If the tension on the urethra is too light as determined during the acute healing phase, the surgeon may grasp and pull on the tie-wrap or suture free ends to shorten the lengths of the tape end portions and thereby increase sling tension. The exposed suture or tie-wrap ends may be severed during chronic implantation.

In yet another approach, tape or sling ends or the end of a tensioning cable coupled to a urethral support mechanism are coupled to a tensioning device that is chronically implanted subcutaneously and can be accessed to adjust sling tension. See, for example, commonly assigned U.S. Pat. Nos. 4,969,892; 5,474,518; and 6,117,067, the entireties of which are herein incorporated by reference. Ratchet or gear mechanisms that are accessed using a driver inserted through the skin and thereby rotated to increase or decrease sling tension are disclosed in the '892 and '518 patents. The adjustment forces are applied to the sling ends and must be transmitted through the sling to effect any change in tension along the sling central portion adjacent the urethra.

Further sling tension adjustment and maintenance techniques involve adding tensioning filaments to the sling free ends and extending the elements through the skin incisions and into engagement with buttons or pads implanted subcutaneously engaging a muscle or rectus fascia layer and/or having tissue engaging elements or anchors along the filament that engage subcutaneous tissues as disclosed, for example, in U.S. Pat. Nos. 6,911,002; 8,518,061; and 8,628,465, the entireties of which are herein incorporated by reference.

SUMMARY

Aspects of devices, systems, and methods are described herein. These aspects may be applied to treat pelvic conditions, such as incontinence, including various forms of fecal incontinence, stress urinary incontinence, urge incontinence, mixed incontinence, etc., pelvic organ prolapse, and like conditions. Various surgical implants, tools, and methods are described in relation to such conditions, each relating to a method for treating the various conditions described herein.

One aspect described herein is an implant comprising: a tissue support portion; an adjustment mechanism; at least one sheath extending from the tissue support portion to the adjustment mechanism; and at least one adjustment element (e.g., a suture) extending through the at least one sheath for engagement with the adjustment mechanism to move the tissue support portion.

The tissue support portion may comprise at least a central portion configured to support a tissue. The tissue support portion may comprise a first end portion and a second end portion, wherein the central portion extends therebetween. The adjustment mechanism may comprise a ratchet. The adjustment mechanism may be within a housing including an inner housing surface and at least one pawl extending therefrom to engage the ratchet. The at least one pawl may comprise three pawls. The ratchet may be reversible. The adjustment mechanism may be removable from the implant. The adjustment mechanism may be actuated by application of a magnetic force to a receiving element in the ratchet (e.g., in the housing). The receiving element may include a metal rod rotatable the adjustment mechanism in response to the magnetic force. The at least one sheath may comprise a compressible portion and a non-compressible portion. The compressible portion may be adjacent the tissue support portion, and the non-compressible portion may extend between the compressible portion and the adjustment mechanism. An exterior portion of any part or section of the implant may be configured to promote or limit tissue growth therewith.

According to one aspect, the adjustment mechanism may be engageable with the adjustment element intra-operatively, i.e., during a surgical procedure, to adjust an aspect of the implant, such as the amount of tension in each adjustment element, and/or the length of a portion of implant, such as a length of an end portion or other portion or piece of an implant. The adjustment element may include any one of a suture, a line, cinch, a strand, a filament, a wire, or the like. Any number of sheaths and/or adjustment elements may be used in this aspect.

Other aspects described herein involve methods of adjusting the implant. One aspect may comprise inserting an implant in the body, the implant including a tissue support portion, a sheath extending from the tissue support portion to an adjustment mechanism, and an adjustment element extending through the sheath for engagement with the adjustment mechanism to move the tissue support portion; placing the tissue support portion in contact with a targeted tissue area; locating the adjustment mechanism remotely from the targeted tissue area to extend the sheath in a treatment direction; and actuating the adjustment mechanism to move the targeted tissue area in the treatment direction.

According to these aspects, the adjustment mechanism may be a ratchet and the actuating step may comprise applying a rotational force to the ratchet. The ratchet may have a receiving element responsive to a magnetic force and the applying step may comprise applying the magnetic force to the receiving element. The tissue may include a bladder tissue, wherein the method may further comprise performing a diagnostic test for the bladder tissue subsequent to the actuating step, and actuating the adjustment mechanism in response to a result of the diagnostic test. These methods may be modified to accommodate the structure or function of any implant or system described herein.

Numerous other aspects of this disclosure also are described. Some aspects involve pelvic implants, including surgical implants (also referred to generally herein as "slings") that include a tissue support portion and two or more end portions extending from the tissue support portion to an adjustment element. Herein, the terms "sling," "implant," and "incontinence sling" without further qualification are used interchangeably. Other aspects include various forms of pelvic implants for supporting different pelvic tissues. In one aspect, a urethral sling may be adapted to be placed through a tissue pathway in a male or female patient so that the tissue support portion is positioned relative to the tissue, for example, below or distal of the urethra or bladder neck (hereafter collectively referred to as the "urethra" for convenience) in a male patient, or above or proximal to the vaginal wall in a female patient, to alleviate urinary incontinence.

Another aspect may be a fecal sling adapted to be placed through a tissue pathway so that the tissue support portion may be positioned inferior to, for example, the anus, the anal sphincter, and/or the lower rectum (hereafter collectively referred to as the "anus" for convenience) to alleviate fecal incontinence. The term "wire" and "suture" may also be used interchangeably to include various forms of a cable or coil structure, such as a suture, a strand, a line, a wire, a filament, a braided version of the aforementioned forms, or the like. The term "adjustment mechanism" may include any structure capable of altering an aspect of the adjustment element, such as the amount tension applied to or the length of the element. Exemplary adjustment mechanisms may include, for example, a ratchet, a one-way grommet, a two-way grommet, or other similar mechanism.

Aspects of the implants described herein may include features or be used according to methods that allow for intra-operative adjustment of an aspect of the body, such as the tension applied to the urethra, anus, or other supported tissue, to enhance efficacy of the implant and method of treatment and for improved patient comfort. Some aspects are applicable to both male and female patients to address issues of urinary and fecal incontinence specific to an anatomical feature of either sex. Exemplary methods for implanting and adjusting the implant also are described. These aspects may include surgical techniques such as forming suprapubic, retropubic, transobturator, "inside-out"

or "outside-in" tissue pathways between two skin incisions, and/or forming a tissue pathway from an incision through the vagina or perineal floor.

In some aspects, sling tension of one or two end portions of the implant may be adjusted by use of an adjustment element and the adjustment mechanism, wherein the mechanism may be located or placed at a location that is accessible intra-operatively or post-operatively.

Multiple (e.g., two) adjustment elements may be used in a coordinated manner in some aspects, meaning that the tension or length of both of the two adjustment elements may be adjusted together. Such coordinated adjustment may allow a surgeon or other user to adjust the placement, length, or tension of an implant. The implant may, for example, be adjusted in a manner that does not cause a urethra or other tissue to become located at a non-anatomical position relative to a midline of the patient. Stated differently, two opposing end portions of an implant can be adjusted together to prevent the urethra or other supported tissue from being moved in a left or a right direction within the patient, which will maintain a correct anatomical position of the urethra or other supported tissue, e.g., at a midline of the patient.

Another aspect is a method of treating a pelvic condition. The method may include implanting a pelvic implant useful to treat a pelvic condition, the implant may include: a tissue support portion, a first end portion, a second end portion, and an adjustment element extending from each of the first end portion and second end portion to an adjustment mechanism. The method may include placing the implant in a patient to support tissue, and adjusting an aspect of the implant with the adjustment mechanism, such as a length of the first or second end portion, by adjusting the adjustment element.

In accordance with some aspects, the implants described herein may permit post-operative adjustment of, for example, the tension applied to the urethra or anus to enhance efficacy and patient comfort. These aspects may be applicable to both males and females to address issues of urinary and fecal incontinence. The implantation methods described herein may include surgical techniques such as: forming suprapubic; retropubic; transobturator; inside out or outside in tissue pathways between two skin incisions; and/or forming a tissue pathway formed from a single incision through the vagina or perineal floor for passage of a the implant therethrough.

Exemplary aspects of some implants may include an adjustment mechanism that is incorporated into or on a section of one or both of the adjustment elements, such as their end portions. The adjustment mechanism may be adjusted during, for example, at least the acute post-operative healing phase to directly adjust tension of the end portions, and indirectly adjust tension of the tissue support portion. The spacing of the adjustment mechanism from the tissue support portion may be selected in relation to the patient's anatomy. For example, the spacing may be selected to facilitate access or engagement with an externally applied adjustment actuator or an actuator element extending percutaneously from a skin incision, and/or to transmit tension along the implant to the tissue support portion. Some adjustment mechanisms are generally adjusted to adjust the length and/or tension of the adjustment element to, for example, tension the center support portion and draw it closer to the urethra or anus, and/or to relax tension of the center support portion to release pressure on the urethra or anus.

In some aspects, the adjustment mechanism may comprise one or more first adjustment elements extending from a point of attachment with an end portion of the tissue support portion, and one or more second adjustment elements coupled to a free end of the one or more first adjustment elements and the adjustment mechanism, such that the free end that may be manipulated to increase or decrease the sling tension.

The adjustment mechanism may be a ratchet mechanism or other mechanism that allow for one-way or two-way adjusting. The ratchet mechanism may be an enclosed implantable device that is inserted into the housing of adjustment mechanism to adjust the adjustment elements by winding each adjustment element around an internal channel in the housing, such as a bobbin. The adjustment mechanism may include a plurality of pawls (e.g., three pawls) that flex outward as the ratchet is turned, allowing clockwise rotation, while preventing counter-clockwise reverse rotation.

In one aspect, the ratchet mechanism may contain a receiving element, such as an inset ferrous metal bar, which may interact with an external magnetic force to actuate the ratchet mechanism (e.g., by rotating the pawls). For example, an external electromagnetic actuator may turn the ratchet by magnetically coupling with the ferrous metal inset. The electromagnet may be contained within a rotatable handle, which may be used to turn the mechanism to control the amount of adjustment. According to this aspect, a magnetic interaction may be used to adjust the implant through the skin without the need for an incision. The ratchet mechanism permits both increasing and decreasing tension. To decrease tension, the ratchet mechanism may have teeth that depress slightly to permit the pawl to move backwards. The ratchet teeth may be depressed by actuating a button located on the adjusting mechanism.

In another aspect, the ratchet mechanism may be actuated physically using an actuation tool (e.g., a hex key) inserted through an incision, or electronically by an implanted battery and/or internal or external actuator.

In still other aspects, the adjustment elements may be implanted within a sheath configured to pull upon the adjustment elements without disrupting surrounding tissue. In some aspects, the sheath may have a compressible portion that allows the adjustment elements to be lengthened or shortened without substantially changing the length of the sheath. The adjustment elements may extend through a non-compressible portion of the sheath that makes it possible to more easily pull upon the adjustment elements. Either the compressible or non-compressible portions of the sheath may be made of a material that is biodegradable in the body and/or a biocompatible.

According to these aspects, the sheath mitigates and minimizes trauma to the patient during post-operative adjustment. During adjustment, the sheath may remain in place, while the adjustment element, or other adjustable material, is adjusted in length. In some aspects, due to tissue ingrowth or implant placement, the only part of the implant that may move relative to the body during adjustment is the apex of the implant that is in contact with the urethra or urethra bulb (e.g., a surface of the tissue support portion).

In some aspects, the adjustment elements are coupled to an adjustment mechanism that is subcutaneously implanted in abutting relation to a supporting tissue (e.g., the lower abdominal muscles above the pubic bone). Post-operative adjustment of sling tension may be achieved by actuating the adjustment mechanism through use of an external adjustment actuator. For convenience, such subcutaneous muscle layers and/or abdominal muscles are simply referred to as "tissue layers" herein.

In some aspects, the adjustment mechanism may comprise a rotatable bobbin that the adjustment elements may extend around. For example, the mechanism may be rotated to release out or draw in a length of the adjustment element, thereby decreasing or increasing sling tension. Altering the length of the adjustment elements may not substantially alter the length of the sheath. Thus, in one aspect, the external adjustment actuator is a tool that is inserted percutaneously (e.g., by penetrating the skin) to engage and actuate the sling adjustment mechanism to, for example, increase or decrease the adjustment spacing. Alternatively, it is possible to dissect down to the adjustment mechanism and directly engage the adjusting tool to adjust the adjustment mechanism. The external adjustment actuator may be an electromagnetic actuator. Various sling tensioning devices are described that may, for example, be rotated by the tool in one direction to draw the end portions together to increase sling tension, and rotated in the other direction to allow the end portions to separate apart to decrease sling tension.

This non-exclusive summary has been presented here simply to point out some of the ways that the described aspects overcomes difficulties presented in the prior art. As such, this summary is intended to distinguish the described aspects from the prior art, and is not intended to operate in any manner as a limitation on the interpretation of any issued claims.

BRIEF DESCRIPTION OF THE DRAWINGS

The accompanying drawings are incorporated in and constitute a part of this specification. These drawings illustrate aspects of the present disclosure that, together with the written descriptions, serve to explain the principles of this disclosure.

DETAILED DESCRIPTION

Aspects of the present disclosure are now described with reference to exemplary implants, tools, devices, systems, and related methods. Some aspects are described with reference to certain medical procedures, such as those used to treat pelvic conditions. Any reference to a particular procedure or condition is provided for convenience and not intended to limit the present disclosure unless claimed. Accordingly, the concepts described herein may be utilized for any analogous procedures—medical or otherwise. As used herein, the terms "comprises," "comprising," or like variation, are intended to cover a non-exclusive inclusion, such that a device or method that comprises a list of elements does not include only those elements, but may include other elements not expressly listed or inherent thereto. Unless stated otherwise, the term "exemplary" is used in the sense of "example" rather than "ideal."

Pelvic floor disorders include urinary and fecal incontinence and pelvic organ prolapse. These disorders typically result from weakness or damage to normal pelvic support systems. Common etiologies include childbearing, removal of the uterus, connective tissue defects, prolonged heavy physical labor and postmenopausal atrophy. Other common etiologies may include prostatectomy sequela, aging, and climacturia.

Procedures for treating urinary incontinence include surgical methods, wherein an implant such as a sling is used to stabilize or support a tissue, such as the bladder neck or urethra. Various different implants and implantation methods are known. These implants and methods may differ based on the type of sling material, the anchoring methods used, the placement of the implant, the methods for placing and supporting the sling, and the type of tissue to be supported. Examples are disclosed in U.S. Pat. Nos. 5,112,344; 5,611,515; 5,842,478; 5,860,425; 5,899,909; 6,039,686; 6,042,534; and 6,110,101, the entireties of which are herein incorporated by reference.

An exemplary implant may include a tissue support portion (or "support portion") that may be used to support a tissue, such as a urethra (including a bladder neck), a bladder, a rectum, a sphincter, or other pelvic tissue. Supporting a "urethra" may include, but is not limited to, supporting any tissue that includes the urethra, the bladder neck, and/or any other tissue adjacent to a urethra (e.g., a bulbospongiosus muscle or a corpus spongiosum). For example, according to some methods involving treatment of urinary incontinence, the support portion may be placed below the bulbospongiosus muscle to support the bulbospongiosus muscle, the corpus spongiosum, and/or the urethra. Alternately, the bulbospongiosus muscle may be dissected and the support portion may be placed incontact with corpus spongiosum tissue to support the corpus spongiosum and/or the urethra.

An exemplary implant additionally may include one or more end portions (otherwise known as an "extension" portion or "arm") attached or attachable to the tissue support portion. Normally, for treating incontinence, an implant may include two opposing end portions. An exemplary end portion may include an elongate piece of material (e.g., a mesh, a molded implant material, a suture, or another biologic material) that extend from the tissue support portion and are connected to the tissue support portion. The end portions are useful to provide support for the tissue support portion and the supported tissue. Generally, for treating incontinence, the two end portions extend from opposite ends of a tissue support portion as elongate "arms" or "extensions." In some aspects, the end portions may attach to supportive tissue in the pelvic region by extending through a tissue path to an internal anchoring point (see, e.g., U.S. Patent Pub. No. US 2010/0256442, the entirety of which is herein incorporated by reference in to this disclosure).

An alternative implant may include two or more end portions extending from opposing sides of the tissue support portion. In exemplary uses, each end portion may extend from the location of attachment with the tissue support portion of the implant to an adjustment element (e.g., a suture). The supportive tissue may be at an end of a tissue path used to perform a desired implant procedure, such as at a location near an external incision in the skin used to perform the procedure. Exemplary locations may be at or near an end of an end portion placed according to a retropubic procedure or a transobturator procedure for placing a sling for treating urinary or fecal incontinence; at a location near tissue of an obturator foramen or rectus fascia; or at a location near a ligament, such as a sacrospinous ligament, etc.

An exemplary implant may include portions, pieces, or sections that are made of a synthetic and/or a biologic material (e.g., porcine, cadaveric, etc.). For example, the end portions may be made of a synthetic material (e.g., a synthetic mesh, such as a polypropylene mesh). The tissue support portion also may be made of a synthetic material (e.g., a polypropylene mesh or a molded material) and/or a biologic material. Examples of implant products that may be similar to those useful according to the present description include those sold commercially by American Medical Systems, Inc., of Minnetonka Minn., under the trade names Spare®, Bioarc®, Monarc®, MiniArc®, InVance®, and AdVance® for treating urinary incontinence.

Another exemplary implant may include supportive portions including or consisting of a tissue support portion, two end portions extending from the tissue support portion, and two adjustment elements extending from each of the two end portions. An implant that has exactly two end portions and two adjustment elements may, for example, be useful for treating urinary or anal incontinence in a male or female patient. The term "supportive portions" refers to portions of an implant that function to support tissue after the implant has been implanted and specifically includes end portions and tissue support portions.

Dimensions of an exemplary tissue support portion may be any dimensions useful to support a specific tissue (e.g., urethral tissue) for treating a pelvic condition (e.g., incontinence). A tissue support portion for use in treating incontinence may be of sufficient length to support and optionally partially surround a urethra or urethra-supporting tissue. A width of a tissue support portion may optionally be greater than a width of end portions. In some aspects, the tissue support portion is sufficiently wide to increase contact area and frictional forces between a tissue support portion and a tissue in contact with the tissue support portion. Exemplary lengths of the tissue support portion may be in the range from 0.5 to 2 inches (1.27 to 5.08 centimeters), such as from 0.75 to 1.5 inches (1.91 to 3.81 centimeters). Exemplary widths of a tissue support portion may be in the range from 0.16 or 0.20 to 1.57 inches (0.4 or 0.5 to 4 centimeters), such as from 0.39 to 0.98 or 1.18 inches (1 to 2.5 or 3 centimeters).

An implant (e.g., sling) for placement against a corpus spongiosum for treatment of urinary incontinence in a male patient may include a widened central support to provide increased contact and frictional engagement with the corpus spongiosum. See, e.g., U.S. Pat. Nos. 7,422,557; 7,914,437; and 8,771,168, the entirety of which is herein incorporated by reference.

Dimensions of the end portions of the tissue support portion and adjustment elements may allow the end portions and the adjustment element to reach between a tissue support portion placed at a first position to support a pelvic tissue, such as tissue of a urethra, vagina, anal sphincter, etc., which may be at an end of the end portion connected to the tissue support portion; and a second location at which the distal end of the end portion attaches to supportive tissue at or about the pelvic region or the adjustment mechanism. These or other lengths will be useful for implants designed to treat other conditions.

One exemplary implant useful for treatment of urinary incontinence is a "mini-sling," or "single incision sling," (e.g., as marketed by American Medical Systems under the trade name MINIARC®). Some aspects described herein are also useful for female incontinence, male incontinence, anal incontinence, and other pelvic conditions. For example, female pelvic floor repair slings may be implanted by techniques that involve transvaginal, transobturator, suprapubic, pre-pubic, or transperineal exposures or pathways. Male urinary incontinence slings may be implanted by techniques that involve transobturator, suprapubic, or transperineal pathways. Some aspects may be useful in treating fecal incontinence e.g., by use of a transvaginal, transobturator, suprapubic or perineal floor pathway. In fecal incontinence applications, other aspects may be used to correct the anorectal angle in the rectum to re-establish continence in patients.

Figure 1:
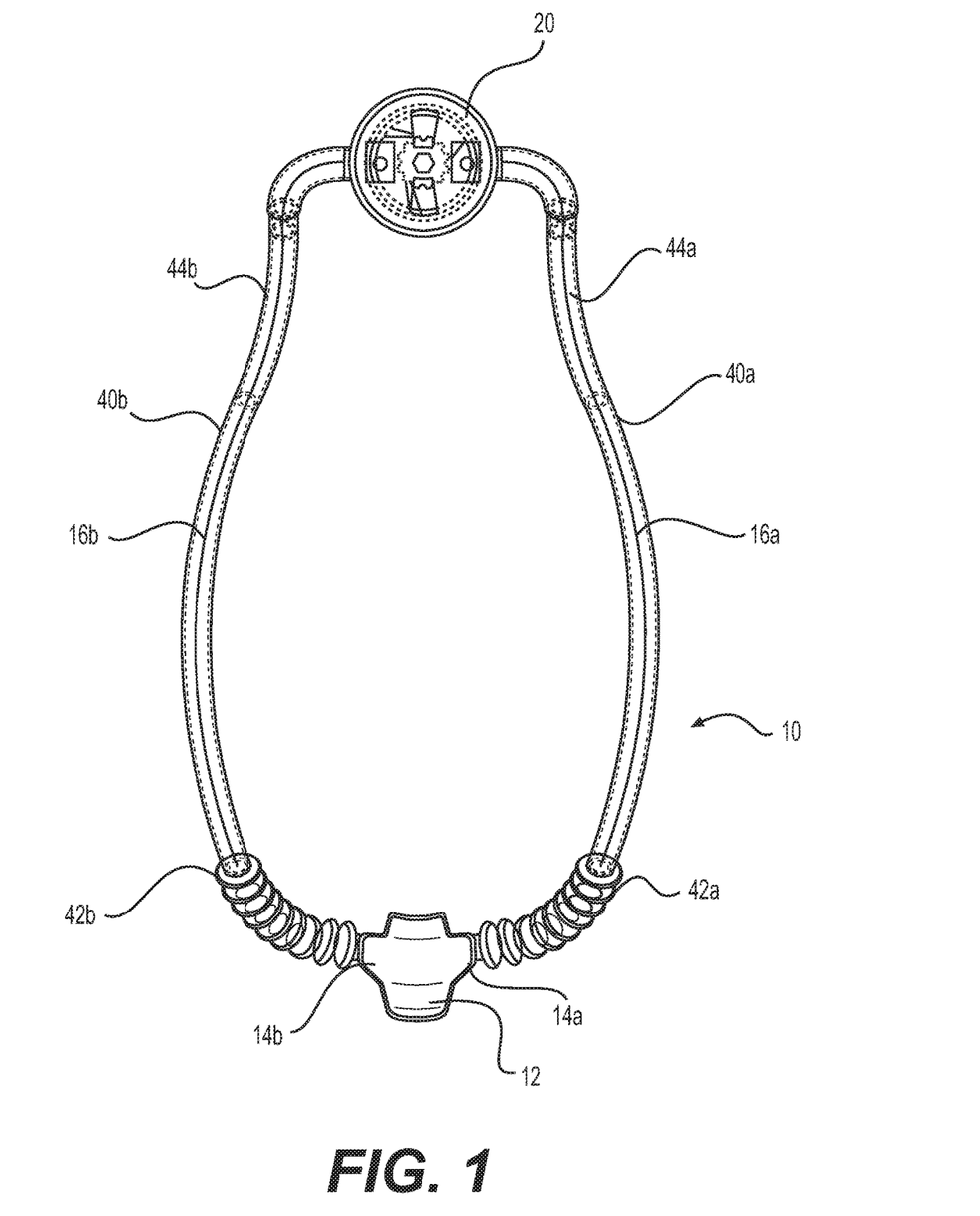
FIG. 1 shows a view of an example implant as described herein.
Figure 3A:
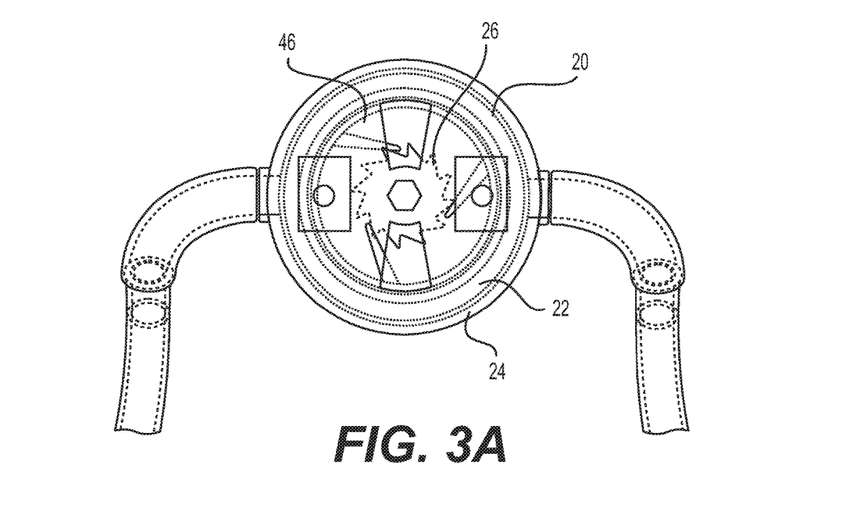
FIGS. 3A and 3B show an example adjustment mechanism as described herein.
Figure 3B:
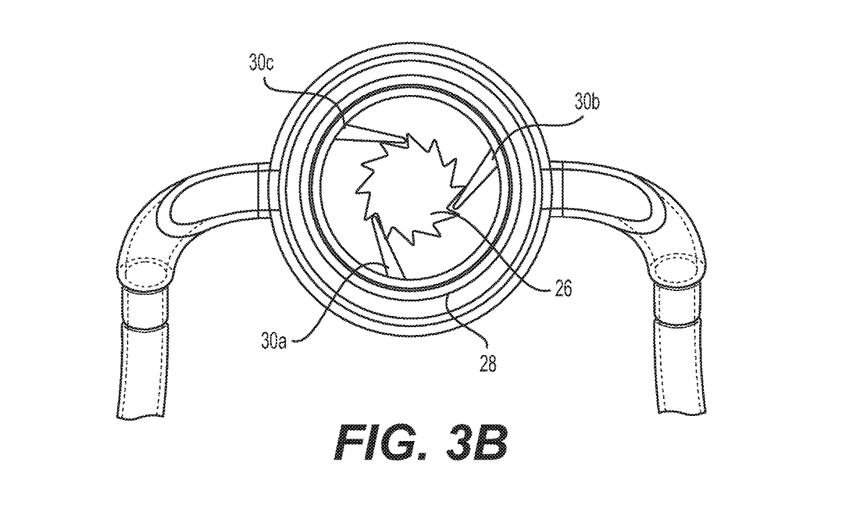

Referring to FIG. 1, an exemplary implant 10 used to treat incontinence and prolapse is depicted. Implant 10 may include a tissue support portion 12 configured to support or reposition a urethra, a bladder neck, an anal sphincter, or other supported tissue. A first end portion 14a and a second end portion 14b extend away from tissue support portion 12 of FIG. 1 to suspend the tissue support portion 12. A first adjustment element 16a (e.g., a suture) extends away from first end portion 14a and a second adjustment element 16b (e.g., another suture) extends away from second end portion 14b. The first adjustment element 16a and second adjustment element 16b may, in some aspects, be operatively coupled to an adjustment mechanism 20 (e.g., as shown in FIGS. 3A-B) that is capable of adjusting a length of the first adjustment element 16a and second adjustment element 16b. The adjustment of the first adjustment element 16a and second adjustment element 16b may translate into adjustment of the length of the adjustment elements 16a, 16b and the position of the tissue support portion 12.

Adjustment element 16 may be a suture, a wire, a braided fiber, or other similar material. Adjustment element 16a, for example, may be a material having a diameter small enough to fit through a first sheath 40a (FIG. 1), and be flexible enough to wind around a portion of adjustment mechanism 20, such as a ratchet mechanism 26 (e.g., FIGS. 3A-B). Adjustment elements 16a and/or 16b may also have an axial loading strength greater than the axial force necessary to reposition the tissue to be supported.

Implant 10 may be implanted by use of any of the methods described herein. Aspects of these methods include pathways through which at least end portions of implant 10 are drawn to dispose tissue support portion 12 in operative relation to a urethra, a bladder neck, an anal sphincter, or other supported tissue. In FIG. 1, for example, each of the first end portion 14a and second end portion 14b, as well as first adjustment element 16a and second adjustment element 16b, are encased in, respectively, a first sheath 40a or a second sheath 40b.

As shown in FIG. 1, the first and second sheaths 40a, 40b extend from each of two opposing end portions 14a, 14b. First sheath 40a extends from a first arm 14a to the adjustment mechanism 20, and second sheath 40b extends from a second arm 14b to the adjustment mechanism. Each sheaths 40a, 40b may be a flexible tube (e.g., a tube made of molded silicon). In some aspects, the sheaths 40a, 40b may have a molded silicon interior layer and a mesh outer layer. The outer layer of the sheaths 40a, 40b may be configured to promote tissue ingrowth, while still allowing the adjustment elements 16 to be adjusted and providing a resistive force as the sling is tightened. For example, the outer layer of sheaths 40a and 40b may be made from any material with a porous structure (e.g., a material with pores greater than 50 μm in size). The first and second adjustment elements 16a, 16b of FIG. 1 extend through the first and second sheaths 40a, 40b. Mesh or other porous material may be attached to the exterior of a non-compressible portion 42a or 42b of the respective first or second sheaths 40a or 40b in a radial or planar manner to provide tissue ingrowth and resistive force. Accordingly, when the first and second adjustment elements 16a and/or 16b are lengthened or shortened, the respective first or second sheaths 40a and/or 40b may not significantly alter in length.

When designed for use in treating urinary incontinence by a single (e.g., medial) incision method, the overall dimensions of implant 10 may vary. For example, implant 10 may be between 2.36 to 5.91 inches (6 to 15 centimeters) in length, in the range from 2.36 to 3.94 inches (6 to 10 centimeters) in length; or 3.15 to 3.94 inches (8 to 10 centimeters) in length; and/or 0.39 to 0.79 inches (1 to 2 centimeters) in width, or 0.39 to 0.59 inches (1 to 1.5 centimeters) in width. Any of these dimension may be realized, for example, at the end portions 14a, 14b. For use as a single-incision sling for treating urinary incontinence, a total length dimension between adjustment mechanism 20 and tissue support portion 12 may be at least sufficient to extend from a location of the lower abdominal muscle below the pubic bone, with tissue support portion 12 placed to support tissue of a urethra. Although not required, the dimensions for an implant 10 configured to treat incontinence by a single incision method may be substantially different than the dimensions of an implant 10 configured to treat a different conditions, or for implantation by a different method.

Figure 2:
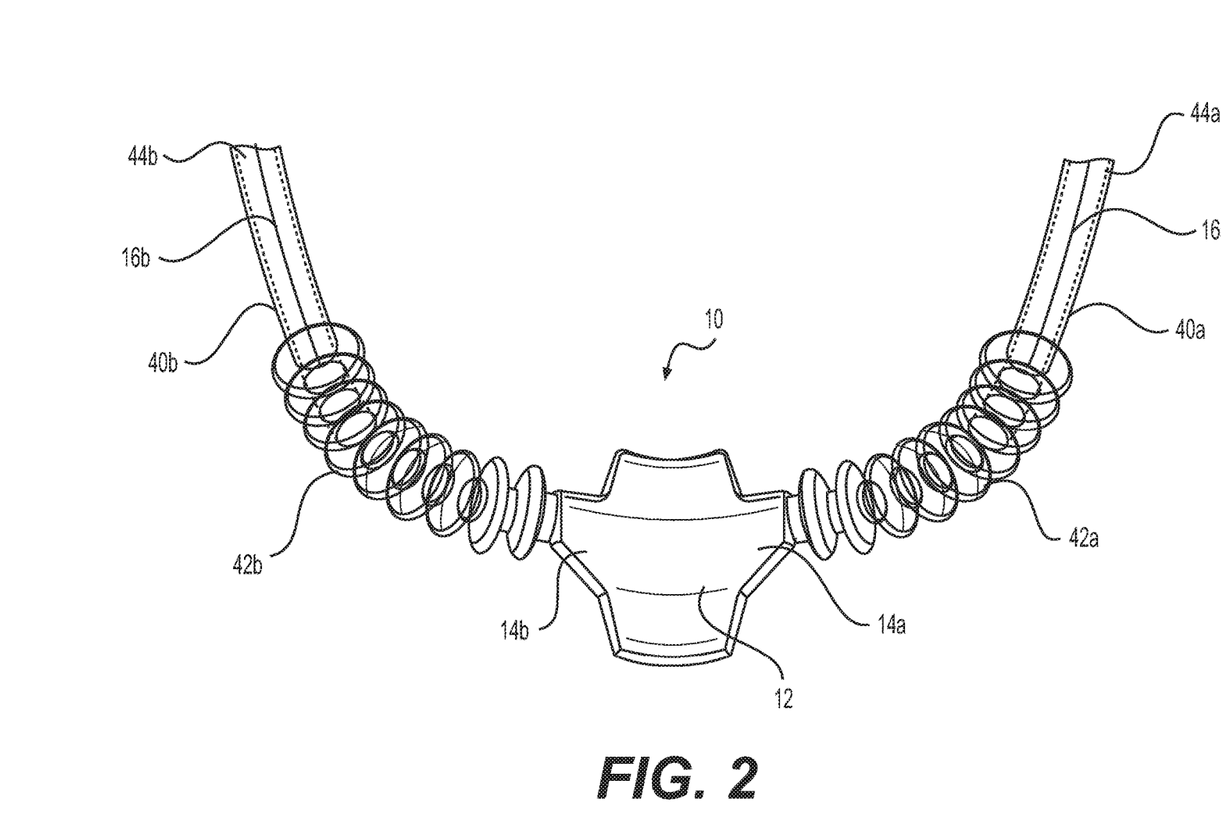
FIG. 2 shows an another view of the implant of FIG. 1.

In some aspects, implant 10 is configured to be implanted and then left in place chronically (e.g., for an extended period of time, or even permanently). Implant 10 may include a mesh or a mesh strip (both being a "mesh") that is elongated, rectangular braided, and/or knitted. Implant 10 may be subdivided into a tissue support portion 12 so that first and second end portions 14a and 14b may be adapted for placement below a tissue to be supported (e.g., a urethra). In FIGS. 1-2, as described above, first end portion 14a extends from a first side of the tissue support portion 12, while second end portion 14b extends from a second side of the tissue support portion 12. In a female patient, support portion 10 may be placed between the urethra or bladder neck and the vaginal wall. End portions 14a and 14b may extend from tissue support portion 12 to opposing adjustment first and second elements 16a, 16b and first and second sheaths 40a, 40b. Although shown in FIGS. 1-2 as being integral, in some aspects, tissue support portion 12 of implant 10 may be formed of different materials, such that the tissue support portion 12 is physically attached to the end portions 14a and 14b and sheaths 40a, 40b.

In some aspects, tissue support portion 12 may be formed of any tissue compatible synthetic material or any natural biocompatible material, including but not limited to treated autologous, allograft, or xenograft tissues, porcine dermis, a tissue engineered matrix, or a combination thereof. It will be understood that implant 10 may alternately be dimensioned and shaped for treatment of male or female urinary or fecal incontinence or to effect pelvic floor, perineal floor, or pelvic prolapse repairs using a variety of surgical approaches.

In other aspects, tissue support portion 12 may include reinforced mesh edges that are configured to form a harness. In this aspect, one of elements 16a or 16b may, for example, be attached to a base of the tissue support portion 12 to exert a force on a central portion of support portion 12 when tightened.

As shown in FIGS. 1-2, each of the first and second sheaths 40a and 40b may, respectively, include a first non-compressible portion 44a or a second non-compressible portion 44b, and a first compressible portion 42a and a second compressible portion 42b, respectively. Each of the first and second compressible portions 42 may be a flexible, compressible tube with an accordion-like configuration, or other similarly compressible configuration. Compressible portions 42a, 42b may, for example, be molded from a flexible silicon or molded latex. The non-compressible portions 44a and 44b of the sheaths 40a and 40b may have a molded silicon interior layer and a mesh outer layer. The outer layer of non-compressible portions 44a and 44b may be configured to promote tissue ingrowth, while still allowing the adjustment elements 16a and 16b to be adjusted in length, and providing a resistive force as the sling is tightened. The outer layer of the non-compressible portions 44a and 44b may be made from any material with a porous structure (e.g., a material having pores greater than 50 μm in size).

With reference to a transvaginal method of treating urinary incontinence, exemplary method steps may include an initial step of placing implant 10, followed by an adjustment step for adjusting one or two lengths of adjustment element 16a, 16b by use of adjustment mechanism 20. An exemplary adjustment mechanism 20 is depicted in FIGS. 3A-B. When mechanism 20 is located at tissue of the abdominal wall, tissue support portion 12 may be located below a urethra, to support the urethra. The surgeon may assess the position, tension, or both, of implant 10 and the supported urethra to determine whether a length of adjustment element 16a, 16b, or both, should be adjusted. If adjustment is necessary, the surgeon may adjust said length by adjusting mechanism 20, which is configured to adjust the length of adjustment element 16a and 16b. Elements 16a and 16b may be adjusted together or individually.

The implants and methods described herein may also be used to treat other pelvic conditions, such as fecal incontinence, in a similar manner. For example, tissue support portion 12 of FIGS. 1-2 may be implanted to extend underneath an anus, an anal sphincter, or an inferior portion of a rectum to correct the anorectal angle in the patient. Multiple surgical approaches may be used to place implant 10 to correct fecal incontinence, including suprapubic, transobturator, retropubic, prepubic, transperineal, and transvaginal. An exemplary method may include a single incision approach performed, for example, transvaginally or transperineally.

As shown in FIGS. 3A-B, adjustment mechanism 20 is incorporated into or on a section of one or both of the adjustment elements 16a and/or 16b. The first and second end portions 14a and 14b are spaced apart from tissue support portion 12 so that implant 10 may be adjusted at least in the acute post-operative phase. The boundary between the tissue support portion 12 and the end portions 14a, 14b is somewhat arbitrary unless the central portion of implant 10 is formed of a different material or has a differing width than the respective material or width of the end portions 14a, 14b. The adjustment mechanism 20 is configured to adjust the length and/or tension of the first and/or second adjustment element 16a, 16b so as to tension the tissue support portion 12 and draw it closer to the urethra or anus. In a similar manner, mechanism 20 is also configured to relax tension of the tissue support portion 12 so as to release pressure on the urethra or anus.

As shown in FIG. 2, and described above, implant 10 comprises tissue support portion 12, first and second end portions 14a, 14b, and first and second adjustment elements 16a, 16b. Adjustment elements 16a, 16b are encased in, respectively, first and second sheaths 40a and 40b. Sheaths 40a, 40b may be any flexible, compressible tube, each having a compressible portion 42a or 42b, which may have an accordion configuration. In FIGS. 1-2, first and second sheaths 40a and 40b extend from their respective compressible portions 42a and 42b at one end to ratchet 26 at an opposite end. One end of the compressible portions 42a or 42b is attached to non-compressible 44a or 44b, while the other end is attached to end portions 14a or 14b. Adjustment elements 16a and 16b may be threaded through sheaths 40a, 40*b* from their respective compressible portions 42*a*, 42*b* and non-compressible portions 44*a*, 44*b*. When the ratchet 26 is actuated, the adjustment elements 16*a*, 16*b* inside the compressible portions 42*a*, 42*b* may change in length, while the sheaths 40*a*, 40*b* do not. In some aspects, a connection mechanism may be provided between end portions 14*a*, 14*b* and compression portion 42*a*, 42*b*. This connection mechanism may be configured to promote the growth of smooth tissue around the tissue support portion 12 to allow for ease of adjustment.

Figure 4A:
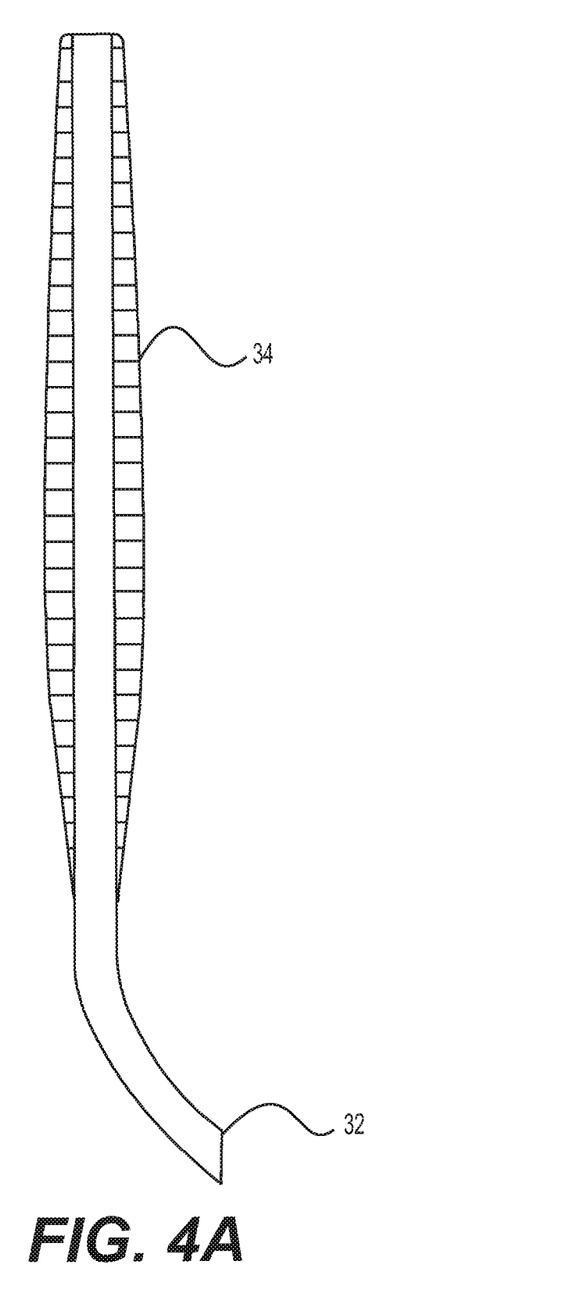
FIGS. 4A and 4B show examples of a sheath as described herein.
Figure 4B:
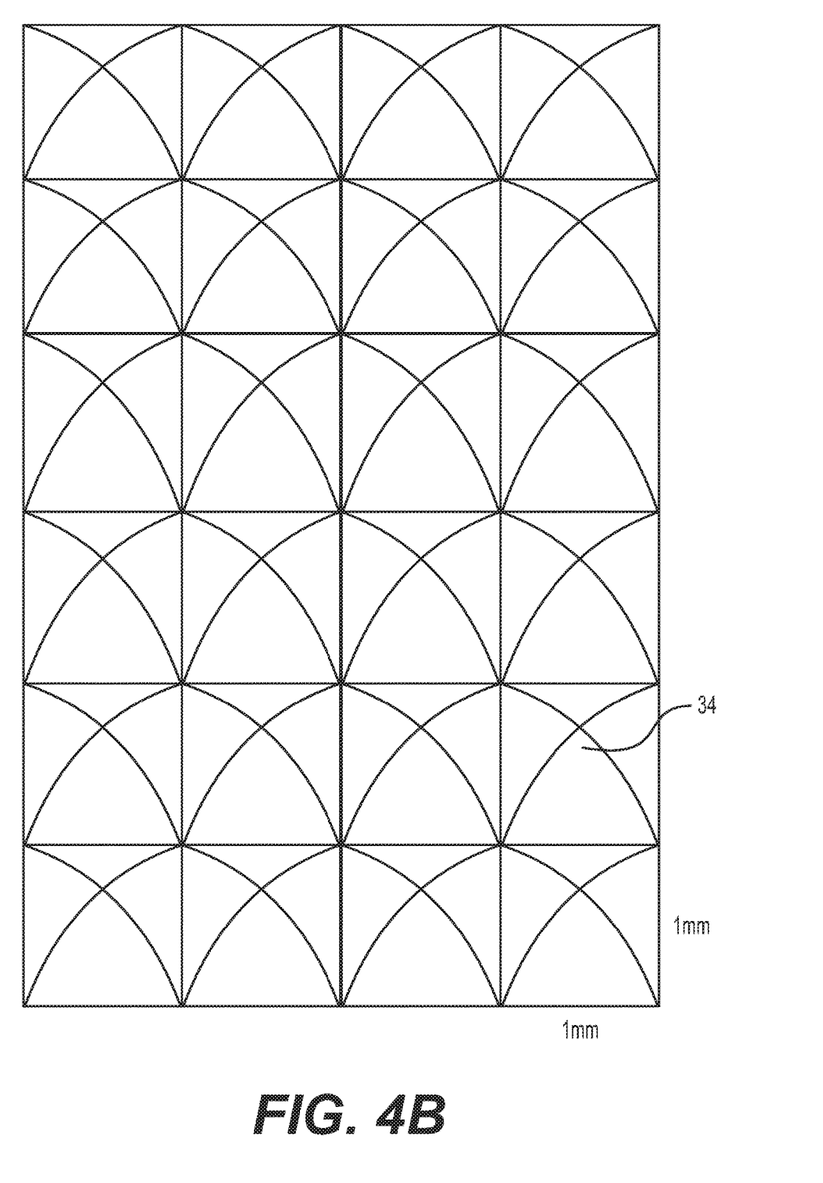

Each of the first and second sheaths 40*a*, 40*b* may be a flexible tube made of, for example, molded silicon. As shown in FIG. 4A, either or both of non-compressible portions 44*a* and/or 44*b* may be encased in a mesh 34 to promote tissue ingrowth and immobilize the sheaths 40*a*, 40*b*, or a single material (e.g., a rubber or a latex). Tissue ingrowth provided by the mesh 34 or other porous material provides a resistive force as the implant 10 is tightened. In some aspects, the mesh may be a 3-dimensional mesh consisting of raised x's arranged in a pattern. For example, as shown in FIG. 4B, the mesh may be arranged around a 0.04 by 0.04 inch (1 mm by 1 mm) grid. The height of the mesh, relative to sheaths 40*a* and 40*b* may decrease near the end attached to compressible portions 42*a* and 42*b*. Alternatively, the mesh may be two-dimensional. Optionally, as shown in FIG. 4A, a biodegradable sheath 32 may be placed over adjustment elements 16*a*, 16*b* to inhibit tissue ingrowth into the mesh 34 and ease adjustment of the implant 10 until, for example, the sheath is absorbed and tissue ingrowth encapsulates and immobilizes implant 10. The biodegradable sheath 32 may be wrapped around at least part of non-compressible portion 44*a*, 44*b*, to promote tissue ingrowth and stabilize and immobilize the sheathing. Alternatively, in this and other folded mesh embodiments disclosed herein, parts of the biodegradable sheath 32 may be coated with a material that inhibits or slows tissue ingrowth, or formed of a material that inhibits or slows tissue ingrowth.

Sheath 40*a* and 40*b* keeps adjustment elements 16*a* and 16*b* enclosed and, thus, isolated from bodily fluids within the interior of the sheaths 40*a*, 40*b*. As shown in FIGS. 3A-B, adjustment mechanism 20 may comprise a top 22, a bottom 24, and ratchet 26. Top 22 and bottom 24 keep ratchet 26 enclosed from bodily fluids.

Adjustment mechanism 20 is configured to increase or decrease sling tension applied to one or both of elements 16*a* and/or 16*b*. The adjustment mechanism 20 may include ratchet 26. The ratchet 26 of FIGS. 3A-B, for example, is an enclosed implantable device that adjusts the adjustment elements 16*a* and 16*b* by winding each element 16*a* or 16*b* around an internal channel 46. An exemplary set of three pawls 30*a*, 30*b*, 30*c* may flex outward as the ratchet 26 is turned, allowing clockwise rotation for forward rotation and preventing counter-clockwise reverse rotation. Any number of pawls may be used.

In some aspects, ratchet 26 of FIGS. 3A-B may contain an inset ferrous metal bar, which may interacts with an external magnetic force to rotate pawls 30*a*, 30*b*, and 30*c*. An external electromagnetic actuator may, for example, turn ratchet 26 by magnetically coupling with the ferrous metal inset. The electromagnet may be contained within a rotatable handle, which may be used to turn the mechanism to control the amount of adjustment. A magnetic interaction may be used through the skin without the need for an incision. In another aspect, ratchet 26 may be actuated physically using a hex key through an incision, or electronically by an implanted battery and external actuator.

In use, ratchet 26 allows a surgeon to post-operatively tension and adjust implant 10. For example, the length of implant 10 may be adjusted from about 0.39 inches (1 cm) to about 2.36 inches (6 cm). To adjust, a standard bladder stress test may be performed on the patient, wherein the patient induces a stress (e.g., by coughing or laughing) and incontinence is observed. A surgeon actuates implant 10 by tightening ratchet 26 until the patient ceases to void when stress is applied.

To actuate mechanism 20 without an incision, an external electromagnetic tool may be used. The electromagnetic device may, for example, be placed on the patient's abdomen to top of a thin sterile barrier located on the skin above the implanted ratchet 26. Ultrasound may also be used to locate ratchet 26. The electromagnetic device may interact with a receiving device of mechanism 20, such as a bar of ferrous material in the implanted device, so that ratchet 26 is actuated as the electromagnetic device turns. To actuate mechanism 20 with an incision, an incision (e.g., a 0.79 inch (2 cm) incision) may be made in the lower abdomen, above the implanted ratchet 26, so that ratchet 26 may be actuated with a tool (e.g., a hex tool).

The disclosed systems, their various components, structures, features, materials and methods may have a number of suitable configurations as shown and described in the previously-incorporated references. Various methods and tools for introducing, deploying, anchoring and manipulate device, implants, and the like as disclosed in the previously-incorporated references are envisioned for use with the present disclosure as well.

All patents, patent applications, and publications cited herein are hereby incorporated by reference in their entirety as if individually incorporated, and include those references incorporated within the identified patents, patent applications and publications.

While principles of the present disclosure are described herein with reference to illustrative aspects for particular applications, the disclosure is not limited thereto. Those having ordinary skill in the art and access to the teachings provided herein will recognize additional modifications, applications, aspects, and substitution of equivalents all fall in the scope of the aspects described herein. Accordingly, the present disclosure is not to be considered as limited by the foregoing description.

The invention claimed is:

1. An implant comprising:
    a tissue support portion;
    an adjustment mechanism;
    at least one sheath extending from the tissue support portion to the adjustment mechanism; and
    at least one adjustment element extending through the at least one sheath for engagement with the adjustment mechanism to move the tissue support portion;
    wherein the adjustment mechanism comprises a ratchet and at least one pawl;
    wherein the adjustment mechanism is actuatable by application of a magnetic force to a receiving element in the ratchet; and
    wherein the receiving element is a metal rod configured to rotate the adjustment mechanism in response to the magnetic force.

2. The implant of claim 1, wherein the tissue support portion comprises at least a central portion configured to support a tissue.

3. The implant of claim 1, wherein the adjustment mechanism is within a housing including an inner housing surface, and the at least one pawl extends therefrom to engage the ratchet.

4. The implant of claim 3, wherein the at least one pawl comprises three pawls.

5. The implant of claim 3, wherein the ratchet is reversible.

6. The implant of claim 1, wherein the adjustment mechanism is removable from the implant.

7. The implant of claim 1, wherein the at least one sheath comprises a compressible portion and a non-compressible portion.

8. The implant of claim 7, wherein the compressible portion is adjacent the tissue support portion, and the non-compressible portion extends between the compressible portion and the adjustment mechanism.

9. An implant comprising:
- a tissue support portion with a first end portion, a second end portion, and a central portion extending therebetween;
- a first sheath extending from the first end portion of the tissue support portion to an adjustment mechanism;
- a second sheath extending from the second end portion of the tissue support portion to the adjustment mechanism; and
- at least one adjustment element extending through the first sheath for engagement with the adjustment mechanism to move the tissue support portion;
- wherein at least one of the first or second sheaths has a compressible portion adjacent the first or second end portions of the tissue support portion, and a non-compressible portion extending from the compressible portion to the adjustment mechanism.

10. The implant of claim 9, wherein the tissue support portion comprises at least a central portion contoured to support a tissue.

11. The implant of claim 9, wherein the adjustment mechanism comprises a ratchet.

12. The implant of claim 9, wherein at least the compressible portion has an external surface configured to promote tissue growth.

13. A method of adjusting an implant, the method comprising:
- inserting an implant into a living body, the implant including a tissue support portion, a sheath extending from the tissue support portion to an adjustment mechanism, and an adjustment element extending through the sheath for engagement with the adjustment mechanism to move the tissue support portion, wherein the adjustment mechanism comprises a ratchet and is actuatable by application of a magnetic force to a metal rod in the ratchet that is configured to rotate the adjustment mechanism in response to the magnetic force;
- placing the tissue support portion in contact with a targeted tissue area;
- locating the adjustment mechanism remotely from the targeted tissue area to extend the sheath in a treatment direction; and
- actuating the adjustment mechanism to move the targeted tissue area in the treatment direction.

14. The method of claim 13, wherein the ratchet has a receiving element responsive to the magnetic force and the application comprises applying a magnetic force to the receiving element.

15. The method of claim 13, wherein the targeted tissue area includes a bladder tissue, the method further comprising performing a diagnostic test for the bladder tissue subsequent to the actuating step, and actuating the adjustment mechanism in response to a result of the diagnostic test.

* * * * *